United States Patent [19]

Volante et al.

[11] Patent Number: 5,290,941

[45] Date of Patent: Mar. 1, 1994

[54] FACILE CONDENSATION OF METHYLBENZOXAZOLES WITH AROMATIC ALDEHYDES

[75] Inventors: Ralph P. Volante, Cranbury; Joseph E. Lynch, Plainfield; Ioannis Houpis, Edison; Audrey Molina, Elizabeth, all of N.J.

[73] Assignee: Merck & Co., Inc., Rahway, N.J.

[21] Appl. No.: 960,623

[22] Filed: Oct. 14, 1992

[51] Int. Cl.$^5$ ............... C07D 413/06; C07D 211/86
[52] U.S. Cl. ................................ 546/270; 546/14; 548/110; 548/217
[58] Field of Search ............ 548/217, 110; 546/14, 546/270

[56] References Cited

FOREIGN PATENT DOCUMENTS 462800 12/1991 European Pat. Off. .

OTHER PUBLICATIONS

Katritzky et al "Heterocyclic Chemistry" Cambridge, p. 53 (1964).
Morrison & Boyd "Organic Chemistry" pp. 179, 714–715 (1976).
Epifani, E. et al., Tetrahedron Letters, vol. 23, No. 50, pp. 6385–6388, (1987).
Sanfilippo, P. J., et al. J. Med. Chem. 31, 1778–1785 (1988).
Dryanska V. et al., Tetrahedron Letters. No. 41, pp. 3519–3320 (1975).
S. B. Lokhande et al., Indian Journal of Chemistry, vol. 25B, pp. 485–488 (1986).
Dryanska, V. et al. Synthesis pp. 37–38 (1976).
Hamana, H. et al., Chemistry Letters, pp. 333–336 (1983).
Jerche, Dietrich von et al., Aus dem Organisch--Chemischen Institut der Universitat Mainz, Eingegangen am Feb. 4, 1958, pp. 171–179.
Skidmore, S., et al., The Quinoline Series, Part I., pp. 1641–1645 (1959). Ried, W., et al., Mitteilung aus dem Institut fur Organische Chemie der Universitat Frankfurt a.M. (Eingegangen am Jul. 14, 1956).
CA 62:5369a (1965).
CA 62:5369a (1965).
CA 61:16210f (1964).
CA61:9617a (1964).
CA61:9617a (1964).
CA 61:8450e (1964).
CA60:14650a (1964).

*Primary Examiner*—C. Warren Ivy
*Assistant Examiner*—Celia Chang
*Attorney, Agent, or Firm*—Roy D. Meredith; Jack L. Tribble

[57] ABSTRACT

An efficient process for the preparation of styrylbenzoxazoles and derivatives thereof comprises reacting a methylbenzoxazole with an aromatic aldehyde in the presence of strong base at low temperature, followed by warming. The condensation products are inhibitors of H+K+-ATPase, and are also useful as penultimate compounds in the preparation of inhibitors of HIV reverse transcriptase.

2 Claims, No Drawings

FACILE CONDENSATION OF METHYLBENZOXAZOLES WITH AROMATIC ALDEHYDES

BACKGROUND OF THE INVENTION

The present invention concerns the condensation of methylbenzoxazole derivatives with aromatic aldehyde derivatives in the presence of strong base at low temperature, followed by warming, to give compounds of formula III.

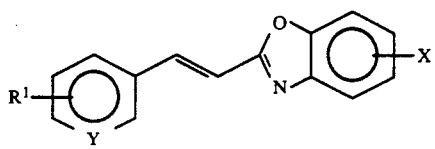

Related compounds are medicinally important enzymes inhibitors, most notably $H^+K^+$-ATPase inhibitors to reduce gastric acid secretion. Simple hydrogenation of pyridinones of III yields compounds which possess HIV reverse transcriptase inhibitory activity.

The synthesis of formula III compounds (hereinafter "styrylbenzoxazoles") occurs via condensation of aromatic aldehydes with methylbenzoxazoles, perhaps by deprotonation of methylbenzoxazole prior to condensation with the aldehyde. In the prior art, related condensations were accomplished under extreme experimental conditions. For example, condensation of benzaldehyde with 2-methylbenzoxazole using potassium methoxide as the catalyst required refluxing of the reaction for 7 hours. This condensation was also achieved using boric acid as the catalyst when the reaction was incubated at about 200° C. when zinc chloride or acetic anhydride was used as the catalyst. In addition to being unsuitable for large scale preparation of products, these condensations afford low to moderate yields of product.

Lokande and Rangnekar developed a more convenient method for the synthesis of styrylbenzoxazoles via condensation of aryl aldehydes with methylbenzoxazole [Ind. J. Chem. 25B, 485 (1986)]. This method employs the use of phase-transfer catalysis by aqueous sodium hydroxide and affords milder reaction conditions, shorter reaction periods and higher yields of styryl product than the previous methodology. This method has features which make it impractical for large scale preparations of styryl products. First, the process is performed in the absence of solvent, and its reaction mixtures are not useful for large scale synthesis. Secondly, the use of phase transfer catalysis affords products of higher impurity than is pharmacologically acceptable. Removal of impurities is expensive and laborious.

More recently, the deprotonation of methylbenzoxazole was accomplished using butyllithium as the catalyst at a temperature of −100° C. [Epifani, E. et al. Tetrah. Lett. 28, 6385 (1987)]. In addition to being operationally difficult on a large scale, the process results in recovery of only the intermediate alcohol adduct. An extra elimination step is required to achieve the desired olefin product. Use of butyllithium methodology is also described in EPO 462800 (e.g. Example 4, Step G).

The existing methodology for the condensation of aldehydes and benzoxazoles has several disadvantages. In addition to requiring operationally difficult temperatures, these methods afford low or modest yields of the olefin product. The prior methods also yield impurities which are expensive to remove. Thus a new direct route to the synthesis of styrylbenzoxazoles of acceptable pharmacological purity would be superior to existing methodology.

The present invention has several advantages over the prior art for making medicinally important compounds. The invention affords greater yields of styrylbenzoxazole products than prior methods. For example, Dryanska and Ivanov report a yield of 72-78% styrylbenzoxazole [Synthesis 37 (1976)]. They report even lower yields in phase transfer catalysis [Tetrah. Lett. 3519 (1975)]. Applicants report a yield of about 95% with the process of the present invention. Another advantage of the present invention is a process that readily affords aromatic aldehydes bearing protons. The novel process of the invention also provides a rapid entry into highly pure styrylbenzoxazoles, while circumventing problematic multistep sequences as required when butyllithium is used as the catalyst in condensation. In addition, the process of the new invention allows conditions which are amendable to large scale production, and obviates the need for additional steps to eliminate impurities. The invention is therefore a more economical, operationally practical, and efficient process for the construction of styrylbenzoxazoles than previous processes. The styrylbenzoxazole compounds useful as intermediates in the preparation of inhibitors of HIV reverse transcriptase. The invention may also provide a direct route to the synthesis of (aryloxy) alkylamines which possess gastric antisecretory activity and are thus useful as drugs in the treatment of ulcers.

SUMMARY OF THE INVENTION

The novel process of the invention is summarized according to Scheme A, wherein an aromatic aldehyde I and a methylbenzoxazole of structural formula II are reacted by treating a solution of I and II with strong base at low temperature, followed by warming. The strong base effects deprotonation of the methylbenzoxazole at the methyl group to afford a reactive methylbenzoxazole anion which then reacts with the carbonyl group of the aldehyde I to give product III. Compounds comprehended by III are themselves useful penultimate compounds for the inhibition of HIV reverse transcriptase.

DETAILED DESCRIPTION OF THE INVENTION

This invention provides a direct, high yielding route to formula III compounds via condensation. The process is represented in Scheme A as the addition of the aldehyde I to a methylbenzoxazole II by treatment with strong alkali metal base at low temperature, followed by warming. Nearly exclusive formation of the styrylbenzoxazole III results.

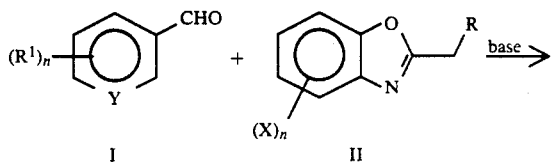

SCHEME A

-continued
SCHEME A

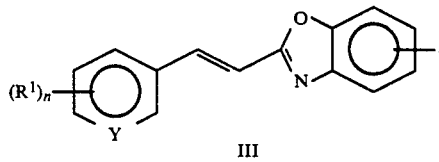

wherein
n is 0–4;
$R^1$ is oxo, $C_{1-4}$alkoxy, aryl $C_{1-4}$alkyloxy, $C_{1-4}$ alkyl unsubstituted or substituted with OH; trimethylsilyloxy, or aryl;
Y is N, S, O or C;
R is H, $C_{1-4}$ alkyl unsubstituted or substituted with oxo or carboxyl; cyano or thioalkyl ether;
X is $C_{1-4}$ alkyl, halo, cyano or thioalkyl ether.

Developing the present invention required the evaluation of various experimental conditions for the condensation reaction. Table I contains a summary of some condensations performed by the applicant in his effort to develop the new methodology. No adduct is detected when tert-BuMgBr, tert-BuOLi, diisopropylamide-MgBr, $PhCH_2NMe_3OMe$ or $PhCH_2NME_3OH$ is used as the catalyst in the reaction, while a mixture of the alcohol and unreacted aldehyde is achieved when lithium bis trimethylsilylamide, or potassium bis trimethylsilylamide is used as the catalyst. Unacceptable levels of impurities are detected in the reaction product when NAOH, tert-BuONa, or Na methoxide is used as the base in the reaction. Some decomposition occurs with lithium tetramethylpiperidide.

TABLE I

Condensation of 2-Methylbenzoxazole 2 with Aldehyde 1

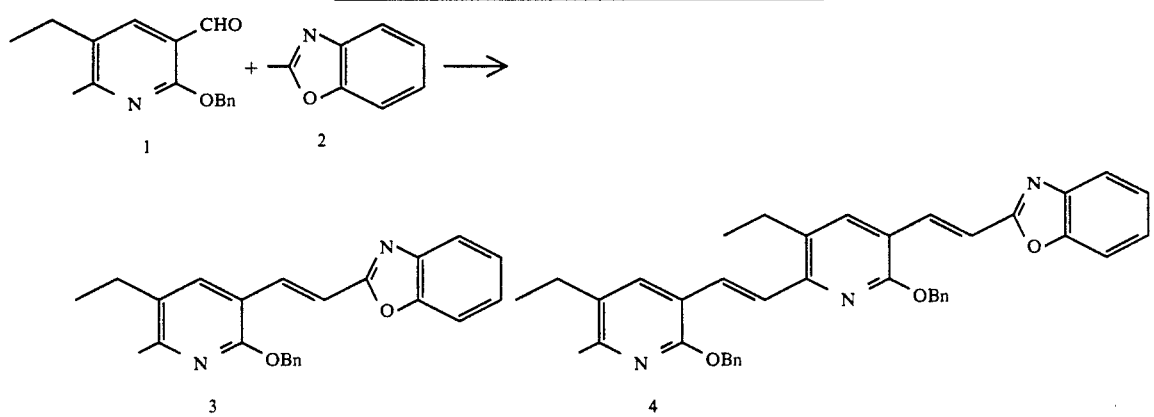

| Entry | Base | Solvent | Temp | Order of Addition & Other Conditions | Results (Ratio 3:4)[1] |
|---|---|---|---|---|---|
| 1 | t-BuOK | THF/tBuOH (3:1) | −15° C. | Base added to 2 for 10 min then 1 added to mixture | Benzoxazole decomposed (Ration 90:10) |
| 2 | t-BuOK | THF/tBuOH (3:1) | −15° C. | Base added to mixture of 1.02 equiv. of 2 & 1 equiv. of 1 for 3 hours. Warm to room temperature | Ratio 98.6:1.4 |
| 3 | t-BuOK | THF/tBuOH (3:1) | −15° C. | Base added to mixture of 1.5 equiv. of 2 & 1 equiv. of 1 for 3 hours. Then room temperature | Ratio varies from 98:2 to 99:1 |
| 4 | t-BuOK | THF/tBuOH | −50° C. | Base added to mixture of 1.5 equiv. of 2 & 1 equiv. of 1 for 3 hours. Then room temperature | Ratio 99.3:0.7 |
| 5 | t-BuOK | THF | −15° C. | Base added to mixture of 1.5 equiv. of 2 & 1 equiv. of 1 for 3 hours. Then room temperature | Level of early impurities increased. Ratio ca. 99:1 |
| 6 | t-BuOK | THF | −78° C. | Base added to mixture of 1.5 equiv. of 2 & 1 equiv. of 1 for 3 hours. Then room temperature | Level of early impurities increased. Ratio ca. 99:1 |
| 7 | t-BuOK | $PhCH_3$ | −50° C. | Add mixture of 2 (1.5 eq) & 1 (1 eq) to base for 2 hours, then room temperature | Mixture difficult to stir. Ratio 99.7:0.3 Other impurities present |
| 8 | t-BuOK | $PhCH_3$/tBuOH (3:1) | −15° C. | Add mixture of 2 (1.5 eq) & 1 (1 eq) to base for 2 hours, then room temperature | 99:1 Several other impurities present impurities present |
| 9 | t-BuOK | $PhCH_3$ | −15° C. | Add mixture of 2 (1.5 eq) & 1 (1 eq) to base for 2 hours, then room temperature | Reaction forms gels even −15° C. Ratio 99.2:0.8 impurities present |
| 10 | KHMDS | THF/$PhCH_3$ | −78° C. | Base added to 2 (1.5 eq) & 1 (1 eq) for 2 hours then quench | Messy reaction >10% of dimer alcohol formed (by NMR) |
| 11 | LHMDS | THF | −30° C. | Add base to 2 & 1 then warm up to 15° C. in 5° C. increments | Complete decomposition of benzoxazole. No adduct formed |
| 12 | t-BuOLi | THF/tBuOH | −15° C. | Add 2 & 1 to base. Warm to room temperature | No reaction. |
| 13 | NaOMe | THF or MeOH | −15° C. | Add 2 & 1 to base. Warm to room temperature | No reaction. Some product at room temperature. Impurities. |

TABLE I-continued

| | | | | | |
|---|---|---|---|---|---|
| 14 | tBuONa | PhCH$_3$ | −15° C. | Add 2 (1.5 equiv) & 1 to base for 30 minutes, warm up to room temperature for 30 hours | Ratio 99.9:0.1 but early eluting impurities present |
| 15 | tBuONa | PhCH$_3$/tBuOH | −15° C. | Add 2 (1.5 equiv) & 1 to base for 30 minutes, warm up to room temperature for 30 hours | Reaction slow; impurities formed >1A % of 4 |
| 16 | t-BuONa | PhCH$_3$/THF | −15° C. | Add 2 (1.5 equiv) & 1 to base for 30 minutes, warm up to room temperature for 30 hours | Ratio 99.7:0.3. Some early eluting impurities are formed |

[1]Ratio 3:4 is the ratio of absorption of species 3 to species 4 as measured by absorption at 210 nm.

The base in the process of the present invention must be a an alkali metal-containing base. Suitable strong bases include lithium tetramethyl piperidide, sodium hydroxide, sodium tert-butoxide, potassium bis trimethylsilylamide, sodium methoxide (at room temperature), and potassium tert-butoxide. The most preferred strong base is potassium tert-butoxide. The strong base may not be lithium tert-butoxide, diisopropylamidemagnesium bromide, tert-butyl magnesium bromide or other bases such as PheCH$_2$NMe$_3$OMe, PheCH$_2$NMe$_3$OH, triethylamine, or diazobicycloundecane (DBU). Preferred alkalimetals in these bases are potassium, sodium, rubidium and cesium; most preferred are potassium and sodium.

Mixing of I and II, followed by addition of strong base is believed to effect formation of the benzoxazole anion of II which then apparently reacts with the carbonyl carbon of aldehyde I to afford the product III. It will be understood that less optimal protocols encompassed by the invention include mixing of reactants in different order, e.g. at −50° C. mixing methylbenzoxazole with base, then adding to the aromatic aldehyde. Other mixing variations will readily occur to a skilled artisan and are equivalents. For example, a mixture of methylbenzoxazole and aromatic aldehyde can be added to base, or base can be added to the mixture.

The process of this invention results in high yielding production of the styrylbenzoxazole III upon warming of the reaction to about room temperature. The reaction of Scheme A is preferably run at low temperature, in the range between about −100° C. and about room temperature. To effect the reaction of the tolyl derivative of I, the temperature range is maintained more preferably at −50° C. to 0° C. Mixing of I and II need not be performed at these lower temperatures, but cooling to these temperatures is preferred before adding the alkali metal-containing base.

In the process of the present invention it is preferable to have one or more equivalents of II for each equivalent of I. Most preferred is about 4 equivalents of II for each equivalent of I. About 1.2 equivalents of base in also most preferred, but a suitable range includes about 0.8 to 1.4 equivalents.

Solvents suitable for use in Scheme A include, e.g., tetrahydrofuran, tetrahydrofuran/tert-butanol, dimethyl sufloxide, DMF, toluene, or hexane. Tetrahydrofuran/tert-butanol is the most preferred solvent. The solvent may also be alcoholic solvents such as tert-butanol, ethanol, and methanol, but these produce a slow reaction with unacceptable levels of impurities.

In the condensation process of the present invention, the ketone group in the pyridinone aldehyde typically requires protection. Many suitable OH protecting groups include but are not limited to benzyoxy, alkoxy or trialkyl silyl groups. Selection, protection and removal of such groups, as well as other protecting groups on I or II, will readily occur to a skilled artisan.

An extensive art exists on protecting groups, e.g. Green, T. W. et al., Protective Groups in Organic Synthesis, John Wiley 1991.

As used herein, Ph stands for phenyl, Bn for benzyl, and Et for ethyl. When any one variable occurs (e.g. R, R$^1$, etc.) more than one time in a molecule, its definition on each occurence is independent of its definition on any other occurrence. The aldehyde is prepared according to EPO 462800 (See, e.g. Examples 4 and 34). The methyl benzoxazole is available commercially.

Thus, in a preferred embodiment of the novel process, methylbenzoxazole is deprotonated with strong alkali-metal base, preferably potassium tert-butoxide, to produce the methyl benzoxazole anion, which reacts with the aldehyde 2-benzyloxy-5-ethyl-6-methylnicotinaldehyde to the produce the olefin 3-[2-(benzoxazol-2-yl)-ethenyl]-5-ethyl-6-methyl-2-benzyloxy-pyridine. Adding the base at room temperature increases the amount of dimer formation. The olefin product is then hydrogenated using Pd/C at warm temperature to yield the product 3-[2-(benzoxazol-2-yl)ethyl]-5-ethyl-6-methyl-2-(1H)-pyridinone. The OH protecting group need not be simultaneously removed in the hydrogenation step, but a preferred embodiment has this advantageous feature.

The experimental representative of the preferred embodiment is detailed below. The procedure is exemplary and should not be construed as being a limitation on the novel process of this invention.

EXAMPLE 1

Large-Scale Preparation of 3-[2-(benzoxazol-2-yl)ethenyl]-5-ethyl-6-methyl-2-benzyloxy-pyridine A solution of the aldehyde 2-benzyloxy-5-ethyl-6-methylnicotinaldehyde (943 g, 3.69 mol) in toluene (2.5L) was diluted with THF (7L) and t-butanol (2.35L). 2-Methylbenzoxazole (1.67L, 4.12 mol) was added and the solution was cooled to about −50° C. in a methanol/dry ice bath. A 1.7M potassium t-butoxide in THF solution (2.7L, 4.6 mol) was added over a period of 1.5 hours at a rate such that the reaction temperature did not exceed −47° C. The reaction mixture was aged at this low temperature for 5 hours, at which time 99% of the aldehyde had been consumed. The reaction was allowed to warm to room temperature and was stirred overnight. The reaction mixture was then added to 10% aqueous NaHCO$_3$. Toluene (8L) was used to rinse the reaction vessel. The reaction mixture was then stirred for 10 minutes and the layers were separated. The organic layer was washed with 10% aqueous NaCl. The organic layer was transferred to a 50L flask and carbon (196 g, pulverized) was added. The mixture was stirred vigorously for 3.5 hours and filtered through diatomaceous earth. The carbon cake was washed with toluene (7.5L) and the filtrate was concentrated in vacuo. The resulting solid was flushed with methanol (5L) and then slurried in methanol (11L) at ambient temperature for 16 hours. The product was collected by filtration, washed with methanol (5L) and dried in vacuo at 40° C. with a nitrogen sweep, yielding the title compound (1078 g), purity=95%.

¹H NMR Spectrum δ in ppm (CDC ): 7.92(d, J=16.4 Hz, 1H); 7.69(m, 1H), 7.58(s, 1H), 7.43–7.21(m,6H), 5.55(s,2H), 2.51(quartet, J=7.6 Hz, 2H), 2.45(s, 3H), 1.1(triplet, 7.6 Hz, 3H).

EXAMPLE 2

Preparation of 3-[2-(benzoxazol-2-yl)ethyl]-5-ethyl-6-methyl-2-(1H)-pyridinone

A. The olefin of Example 1 (1.3 kg) was slurried in methanol (8 L) and transferred to a 5 gal autoclave using additional methanol (8 L) as rinse. The catalyst, 260 g of 5% Pd/C (50 wt % water) was charged and the hydrogenation was allowed to proceed at 50° C., 45 psig until hydrogen uptake was complete and the reaction was judged complete by LC analysis (olefin reactant undectable).

B. Additional Batches

The reaction mixture was removed from the autoclave and a second batch was charged. After completion of the third batch (3.9 kg total) the autoclave was rinsed with methanol (20 L). Each batch was filtered through a bed of solka-floc followed by the rinse, and the filter cake was rinsed with methanol (8 L).

Each 20 L portion of the filtrate was checked for insoluble material (300 mL disk <#1). Once it was established that it was clear, the filtrate was concentrated to a slurry (total vol 25 L). The slurry was warmed to 30° C. and a sample of solid was submitted for x-ray analysis. X-ray analysis indicated that the crystal form was the undesired form II. The batch was allowed to stir overnight and then was cooled to 20° C. X-ray then showed the correct form I; water (50 L) was added slowly, the slurry was aged for 1 to 2 h at ambient temperature, and was then filtered. The cake was washed with 1:2 methanol:water (18 L), sucked dry under nitrogen for 2 h and then dried i-n vacuo at 45° C. for 30 h (Yield 99.4%).

The dry solid (2.523 kg) was passed through an alpine mill to give the desired particle size (95% <25 microns).

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. The process of synthesizing the product compound 3-[2-(benzoxazol-2-yl)ethenyl]-5-ethyl-6-methyl-2-benzoxy-pyridine of the structure

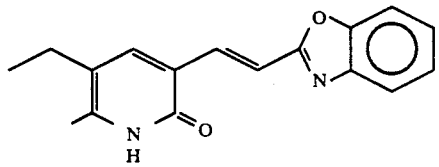

comprising the step of
  (a) mixing about four equivalents of 2-methylbenzoxazole with about one equivalent of 2-benzoxy-5-ethyl-6-methylnicotinaldehyde, yielding a mixture;
  (b) mixing, at a temperature of about −50° C., said mixture with about 1.2 equivalents of potassium tert-butoxide;
  (c) warming the reaction mixture to give the product compound
said process having a yield of 95% or greater.

2. The process of synthesizing the product compound 3-[2-(benzoxazol-2-yl-ethyl]-5-ethyl-6-methyl-2-(1H)-pyridinone, of the structure

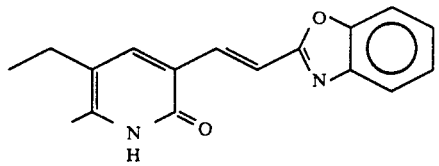

comprising the steps of
  (a) mixing about four equivalents of 2-methylbenzoxazole with about one equivalent of 2-benzoxy-5-ethyl-6-methylnicotinaldehyde, yielding a mixture;
  (b) mixing, at a temperature of about −50° C., said mixture with about 1.2 equivalents of potassium tert-butoxide;
  (c) warming the reaction mixture to give the olefin intermediate compound; and
  (d) hydrogenating to give the product compound,
the steps of (a)–(c) having an overall yield of 95% or greater.

* * * * *